(12) United States Patent
Mestha et al.

(10) Patent No.: US 10,219,739 B2
(45) Date of Patent: Mar. 5, 2019

(54) BREATHING PATTERN IDENTIFICATION FOR RESPIRATORY FUNCTION ASSESSMENT

(71) Applicant: Xerox Corporation, Norwalk, CT (US)

(72) Inventors: Lalit K. Mestha, Fairport, NY (US); Eribaweimon Shilla, Shillong (IN); Edgar A. Bernal, Webster, NY (US); Graham Stephen Pennington, Webster, NY (US); Himanshu Jayantkumar Madhu, Mumbai (IN)

(73) Assignee: Xerox Corporation, Norwalk, CT (US)

( * ) Notice: Subject to any disclaimer, the term of this patent is extended or adjusted under 35 U.S.C. 154(b) by 262 days.

(21) Appl. No.: 14/553,659

(22) Filed: Nov. 25, 2014

(65) Prior Publication Data

US 2015/0094597 A1 Apr. 2, 2015

Related U.S. Application Data

(63) Continuation of application No. 14/044,043, filed on Oct. 2, 2013.

(51) Int. Cl.
*A61B 5/00* (2006.01)
*A61B 5/11* (2006.01)
(Continued)

(52) U.S. Cl.
CPC .......... *A61B 5/4818* (2013.01); *A61B 5/0075* (2013.01); *A61B 5/0077* (2013.01);
(Continued)

(58) Field of Classification Search
None
See application file for complete search history.

(56) References Cited

U.S. PATENT DOCUMENTS 6,062,216 A * 5/2000 Corn .................. A61B 5/113
128/204.23
6,290,654 B1 9/2001 Karakasoglu
(Continued)

FOREIGN PATENT DOCUMENTS

WO WO 2012/140531 10/2012

OTHER PUBLICATIONS

Wentz, Thomas, et al. "Accuracy of dynamic patient surface monitoring using a time-of-flight camera and B-spline modeling for respiratory motion characterization." Physics in medicine and biology 57.13 (2012): 4175.*

(Continued)

*Primary Examiner* — Patricia Mallari
*Assistant Examiner* — Jairo Portillo

(57) ABSTRACT

What is disclosed is a system and method for identifying a patient's breathing pattern for respiratory function assessment without contact and with a depth-capable imaging system. In one embodiment, a time-varying sequence of depth maps are received of a target region of a subject of interest over a period of inspiration and expiration. Once received, the depth maps are processed to obtain a breathing signal for the subject. The subject's breathing signal comprises a temporal sequence of instantaneous volumes. One or more segments of the subject's breathing signal are then compared against one or more reference breathing signals each associated with a known pattern of breathing. As a result of the comparison, a breathing pattern for the subject is identified. The identified breathing pattern is then used to assess the subject's respiratory function. The teachings hereof find their uses in an array of diverse medical applications. Various embodiments are disclosed.

16 Claims, 16 Drawing Sheets

(51) Int. Cl.
*A61B 5/113* (2006.01)
*A61B 5/107* (2006.01)

(52) U.S. Cl.
CPC ............ *A61B 5/1073* (2013.01); *A61B 5/113* (2013.01); *A61B 5/1128* (2013.01); *A61B 5/6898* (2013.01); *A61B 5/7203* (2013.01); *A61B 5/7246* (2013.01); *A61B 5/7264* (2013.01); *A61B 5/7282* (2013.01); *A61B 5/742* (2013.01); *A61B 5/0013* (2013.01); *A61B 5/0022* (2013.01); *A61B 5/746* (2013.01); *A61B 5/747* (2013.01); *A61B 2576/00* (2013.01)

(56) References Cited

U.S. PATENT DOCUMENTS

| | | | |
|---|---|---|---|
| 8,790,269 B2 | 7/2014 | Xu et al. | |
| 8,792,969 B2 | 7/2014 | Bernal et al. | |
| 8,971,985 B2 | 3/2015 | Bernal et al. | |
| 9,141,868 B2 | 9/2015 | Xu et al. | |
| 9,155,475 B2 | 10/2015 | Xu et al. | |
| 9,226,691 B2 | 1/2016 | Bernal et al. | |
| 9,301,710 B2 | 4/2016 | Mestha et al. | |
| 9,504,426 B2 | 11/2016 | Kyal et al. | |
| 2003/0009091 A1 | 1/2003 | Edgar, Jr. et al. | |
| 2003/0164172 A1* | 9/2003 | Chumas | A61B 90/13 128/898 |
| 2004/0111040 A1 | 6/2004 | Ni | |
| 2004/0254773 A1* | 12/2004 | Zhang | A61B 5/1135 703/11 |
| 2006/0214949 A1* | 9/2006 | Zhang | G06T 15/10 345/629 |
| 2007/0276278 A1 | 11/2007 | Coyle | |
| 2008/0159591 A1 | 7/2008 | Ruedin | |
| 2008/0275349 A1 | 11/2008 | Halperin | |
| 2009/0062696 A1* | 3/2009 | Nathan | A61B 5/1107 600/595 |
| 2010/0063419 A1 | 3/2010 | Mostafavi et al. | |
| 2010/0130873 A1* | 5/2010 | Yuen | A61B 5/0205 600/484 |
| 2010/0217158 A1* | 8/2010 | Wolfe | A61B 5/113 600/595 |
| 2011/0040217 A1 | 2/2011 | Centen | |
| 2011/0144517 A1 | 6/2011 | Cervantes | |
| 2011/0166408 A1* | 7/2011 | Sumanaweera | A61N 5/103 600/1 |
| 2011/0190598 A1* | 8/2011 | Shusterman | G06Q 50/22 600/301 |
| 2011/0251493 A1 | 10/2011 | Poh et al. | |
| 2011/0313327 A1* | 12/2011 | Van Acht | A61B 5/11 600/595 |
| 2012/0195473 A1 | 8/2012 | De Haan et al. | |
| 2012/0229607 A1* | 9/2012 | Baker | H04N 13/221 348/46 |
| 2012/0296343 A1* | 11/2012 | Bodduluri | A61F 2/10 606/133 |
| 2013/0053718 A1* | 2/2013 | Hung | A61B 5/486 600/534 |
| 2013/0124148 A1* | 5/2013 | Jin | G06F 17/5086 703/1 |
| 2013/0144190 A1* | 6/2013 | Bruce | A61B 5/4818 600/586 |
| 2013/0324874 A1 | 12/2013 | Bernal et al. | |
| 2015/0073281 A1 | 3/2015 | Mestha et al. | |
| 2015/0094606 A1 | 4/2015 | Mestha et al. | |
| 2015/0245787 A1 | 9/2015 | Kyal et al. | |

OTHER PUBLICATIONS

Chen, Huijun, et al. "Color structured light system of chest wall motion measurement for respiratory volume evaluation." Journal of biomedical optics 15.2 (2010): 026013-026013.*

Aliverti, Andrea, et al. "Optoelectronic plethysmography in intensive care patients." 2000, American journal of respiratory and critical care medicine 161. 5: 1546-1552.

Nozoe, Masafumi, Kyoshi Mase, and Akimitsu Tsutou, "Regional Chest Wall Volume Changes During Various Breathing Maneuvers in Normal Men.", 2011, Journal of the Japanese Physical Therapy Association 14/1: 12-18.

Sharifahmadian et al. "Adaptive signal processing algorithm for remote detection of heart rate using UWB waveforms based on principal component analysis", IEEE conference, Sep. 2-6, 2009.

Tan et al. "Real time vision based respiration monitoring system", IEEE 2010.

Yu Sun et al., "Motion-compensated noncontact imaging photoplethysmography to monitor cardiorespiratory status during exercise", J. of Biomed. Optics vol. 16 No. 7 (Jul. 2011). pp. 77010-1-77010-9.

Min-Zher Poh et al., "Non-contact, automated cardiac pulse measurements using video imaging and blind source separation", Optical Express vol. 18 No. 10 (May 7, 2010). pp. 10762-10774.

Giovanni Cennini et al., "Heart rate monitoring via remote photoplethysmography with motion artifacts reduction", Optical Express vol. 18 No. 5 (Mar. 1, 2010). pp. 4867-4875.

Lorenzo Scalise, "Non contact heart monitoring", InTech Open Access, Chapter 4 (Jan. 2012). 27 Pages.

* cited by examiner

BREATHING PATTERN IDENTIFICATION FOR RESPIRATORY FUNCTION ASSESSMENT

CROSS-REFERENCE TO RELATED APPLICATIONS

This application is a continuation-in-part of co-pending U.S. patent application Ser. No. 14/044,043, filed on Oct. 2, 2013, entitled BREATHING PATTERN IDENTIFICATION FOR RESPIRATORY FUNCTION ASESSMENT, which is hereby incorporated by reference in its entirety.

TECHNICAL FIELD

The present invention is directed to systems and methods for identifying a patient's breathing pattern for respiratory function assessment.

BACKGROUND

Monitoring respiratory events is of clinical importance in the early detection of potentially fatal conditions. Current technologies involve contact sensors the individual must wear which may lead to patient discomfort, dependency, loss of dignity, and further may fail due to a variety of reasons. Elderly patients and neonatal infants are even more likely to suffer adverse effects of such monitoring by contact sensors. Unobtrusive, non-contact methods are increasingly desirable for patient respiratory function assessment.

Accordingly, what is needed are systems and methods for identifying a patient's breathing pattern for respiratory function assessment without contact and with a depth-capable imaging system.

INCORPORATED REFERENCES

The following U.S. Patents, U.S. Patent Applications, and Publications are incorporated herein in their entirety by reference.

"Processing A Video For Tidal Chest Volume Estimation", U.S. patent application Ser. No. 13/486,637, by Bernal et al. which discloses a system and method for estimating tidal chest volume by analyzing distortions in reflections of structured illumination patterns captured in a video of a thoracic region of a subject of interest.

"Minute Ventilation Estimation Based On Depth Maps", U.S. patent application Ser. No. 13/486,682, by Bernal et al. which discloses a system and method for estimating minute ventilation based on depth maps.

"Minute Ventilation Estimation Based On Chest Volume", U.S. patent application Ser. No. 13/486,715, by Bernal et al. which discloses a system and method for estimating minute ventilation based on chest volume by analyzing distortions in reflections of structured illumination patterns captured in a video of a thoracic region of a subject of interest.

"Processing A Video For Respiration Rate Estimation", U.S. patent application Ser. No. 13/529,648, by Bernal et al. which discloses a system and method for estimating a respiration rate for a subject of interest captured in a video containing a view of that subject's thoracic region.

"Respiratory Function Estimation From A 2D Monocular Video", U.S. patent application Ser. No. 13/630,838, by Bernal et al. which discloses a system and method for processing a video acquired using an inexpensive 2D monocular video acquisition system to assess respiratory function of a subject of interest.

"Monitoring Respiration with a Thermal Imaging System", U.S. patent application Ser. No. 13/103,406, by Xu et al. which discloses a thermal imaging system and method for capturing a video sequence of a subject of interest, and processing the captured images such that the subject's respiratory function can be monitored.

"Enabling Hybrid Video Capture Of A Scene Illuminated With Unstructured And Structured Illumination Sources", U.S. patent application Ser. No. 13/533,605, by Xu et al. which discloses a system and method for enabling the capture of video of a scene illuminated with unstructured and structured illumination sources.

"Contemporaneously Reconstructing Images Captured Of A Scene Illuminated With Unstructured And Structured Illumination Sources", U.S. patent application Ser. No. 13/533,678, by Xu et al. which discloses a system and method for reconstructing images of a scene being illuminated with unstructured and structured illumination sources.

"Respiratory Physiology: The Essentials", John B. West, Lippincott Williams & Wilkins; $9^{th}$ Ed. (2011), ISBN-13: 978-1609136406.

BRIEF SUMMARY

What is disclosed is a system and method for identifying a patient's breathing pattern for respiratory function assessment without contact and with a depth-capable imaging system. In one embodiment, a time-varying sequence of depth maps is received of a target region of a subject of interest over a period of inspiration and expiration. The depth maps are processed to obtain a breathing signal for the subject which comprises a temporal sequence of instantaneous volumes across time intervals during inspiratory and expiratory breathing. One or more segments of the breathing signal are then compared against reference breathing signals, each associated with a known pattern of breathing. As a result of the comparison, a breathing pattern for the subject is identified. The identified breathing pattern is used to assess the subject's respiratory function. The teachings hereof find their uses in a wide array of medical applications.

Many features and advantages of the above-described system and method will become apparent from the following detailed description and accompanying drawings.

BRIEF DESCRIPTION OF THE DRAWINGS

The foregoing will be made apparent from the following detailed description taken in conjunction with the accompanying drawings.

DETAILED DESCRIPTION

What is disclosed is a system and method for identifying a patient's breathing pattern for respiratory function assessment without contact and with a depth-capable imaging system.

Non-Limiting Definitions

A "subject of interest" refers to a person being monitored for respiratory function assessment. It should be appreciated that the use of the terms "human", "person", or "patient" herein is not to be viewed as limiting the scope of the appended claims solely to human subjects.

Figure 1:
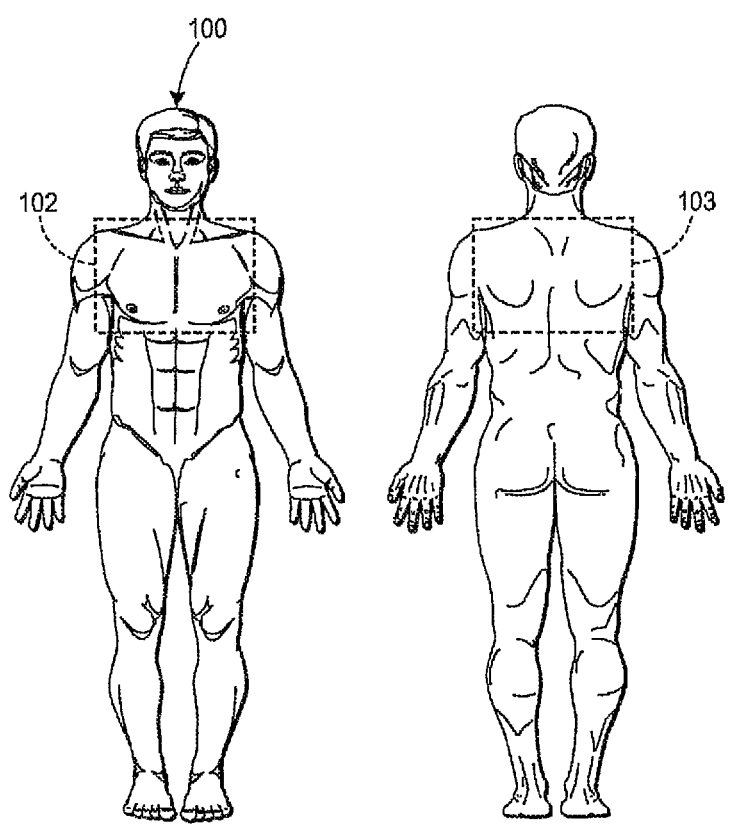
FIG. 1 shows an anterior (front) view and a posterior (back) view of a subject of interest intended to be monitored for respiratory function assessment in accordance with the teachings hereof.

A "target region" refers to an area or region of the subject where respiratory function can be assessed. For example, the target region may be a subject's anterior thoracic region, a region of the subject's dorsal body, and/or a side view containing the subject's thoracic region. It should be appreciated that a target region can be any view of a region of the subject's body which can facilitate respiratory function assessment. FIG. 1 shows an anterior (frontal) view which outlines a target region 102 comprising the subject's anterior thoracic region. Target region 103 is of the subject's posterior thoracic region.

"Respiration", as is normally understood, is a process of inhaling of air into lungs and exhaling air out of the lungs followed by a post-expiratory pause. Inhalation is an active process caused by a negative pressure having been induced in the chest cavity by the contraction of a relatively large muscle (often called the diaphragm) which changes pressure in the lungs by a forcible expansion of the lung's region where gas exchange takes place (i.e., alveolar cells). Exhalation is a passive process where air is expelled from the lungs by the natural elastic recoil of the stretched alveolar cells. The lining of alveolar cells has a surface-active phospholipoprotein complex which causes the lining of the lungs to naturally contract back to a neutral state once the external force causing the cell to stretch is released. A post-expiratory pause occurs when there is an equalization of pressure between the lungs and the atmosphere.

"Inspiration" occurs when the subject forces the expansion of the thoracic cavity to bring air into their lungs. A maximally forced inspiratory breath is when the subject cannot bring any more air into their lungs.

"Expiration" is when the subject forces the contraction of the thoracic cavity to expel air out of their lungs. A maximally forced expiratory breath is when the subject cannot expel any more air from their lungs.

Figure 2:
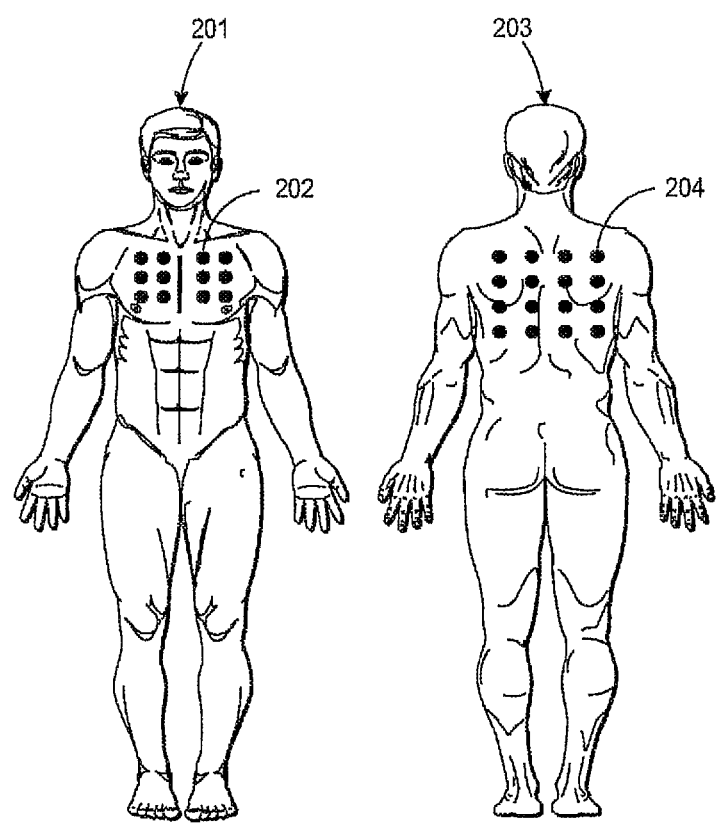
FIG. 2 shows the subject of FIG. 1 having a plurality of reflective marks arrayed in a uniform grid on their anterior thoracic region and on their posterior thoracic region.
Figure 3:
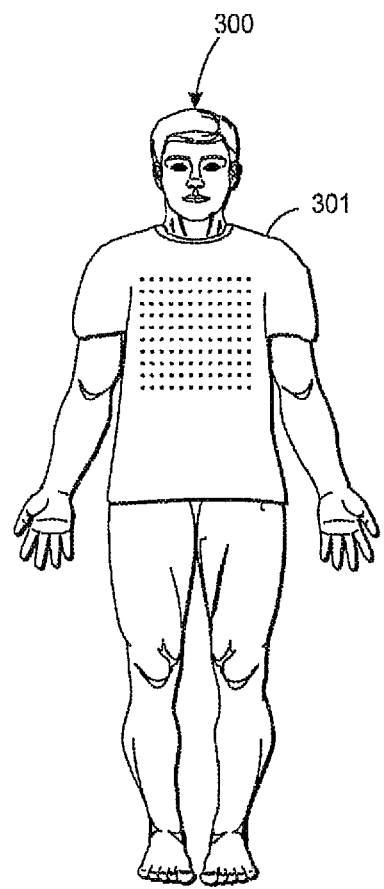
FIG. 3 shows the subject of FIG. 1 wearing a shirt with a uniform pattern of reflective dots arrayed in uniform grid with a one inch dot pitch along a horizontal and a vertical direction.

"Depth map sequence" is a reconstructed temporal sequence of 3D surface maps of a target region of a subject. There is a plurality of techniques known in the art for obtaining a depth map of a target region. For example, a depth map may be constructed based on the amount of deformation in a known pattern comprising, for instance, structured patterns of light projected onto the target region, textural characteristics present on the target region itself such as skin blemishes, scars, markings, and the like, which are detectable by a video camera's detector array. FIG. 2 shows a subject of interest 201 having a plurality of reflective marks arrayed in a uniform pattern 202 on an anterior thoracic region. Subject 203 is shown having a plurality of emissive marks such as LEDs arrayed in a uniform pattern 204 on their posterior thoracic region. The pattern may alternatively be an array of reflective or emissive marks imprinted or otherwise fixed to an item of clothing worn by the subject which emit or reflect a wavelength range detectable by sensors in a video camera's detector array. Reflective marks may be dots of reflective tape, reflective buttons, reflective fabric, or the like. Emissive marks may be LED illuminators sewn or fixed to the shirt. In FIG. 3, subject 300 is shown wearing shirt 301 with a uniform pattern of reflective dots arrayed in uniform grid with a 1 inch dot pitch along a horizontal and a vertical direction. It should be appreciated that the pattern may be a uniform grid, a non-uniform grid, a textured pattern, or a pseudo-random pattern so long as the pattern's spatial characteristics are known apriori. Higher-resolution patterns are preferable for reconstruction of higher resolution depth maps. Depth maps may be obtained from video images captured using an image-based depth sensing device such as an image-based depth sensing device comprising any of: a red green blue depth (RGBD) camera, an infrared depth camera, a passive stereo camera, an array of cameras, an active stereo camera, and a 2D monocular video camera. Depth maps may also be obtained from data acquired by non-image-based depth sensing devices such as a LADAR device, a LiDAR device, a photo wave device, or a time-of-flight measurement device as a depth measuring system. Depth maps can be obtained from data obtained by any of a wide variety of depth-capable sensing devices or 3D reconstruction techniques.

"Receiving depth maps" is intended to be widely construed and includes to download, upload, estimate, measure, obtain, or otherwise retrieve from a memory, hard drive, CDROM, or DVD. The depth maps are measured with a depth-capable sensing device. It should be appreciated that depth maps can be obtained using a camera to capture images of the subject while illuminated by a projected pattern of structured light, the camera being sensitive to a wavelength range of the structured light. The depth maps are then generated based upon a comparison of spatial characteristics of reflections introduced by a movement in the subject's chest cage to known spatial characteristics of the projected patterns in conjunction with the known distance between the light projector and the camera, and using the characterized distortions at different locations to calculate the depth map for each image in the video. Such a method is taught in the above-incorporated reference by Bernal et al. Depth maps can be generated using distortions in patterned clothing worn by the subject as taught in the above-incorporated reference by Bernal et al. The embodiments herein are discussed with respect to the patterned clothing embodiment.

A "reference breathing signal" refers to a volume signal that is associated with a known pattern of breathing. By a comparison of one or more segments of the subject's breathing signal against reference breathing signals which are associated with known breathing patterns, a pattern can be identified for the subject's breathing. The reference breathing signal can be retrieved from, for example, a memory, a storage device such as a hard drive or removable media, or received from a remote device over a wired or wireless network. The reference breathing signal may be volume signals generated using the depth capable sensor in a simulated environment by a respiratory expert. It can also be generated using the depth capable sensor on patients with identified respiratory diseases.

A "subject's breathing signal" refers to a temporal sequence of instantaneous volumes across time intervals during a period of an inspiratory and an expiratory breathing. Instantaneous volumes are obtained from processing the depth maps. In one embodiment, the depth map comprises a 3D hull defined by a set of 3D coordinates namely their horizontal, vertical and depth coordinates (x, y and z respectively). Points in the hull can be used to form a triangular tessellation of the target area. By definition of a tessellation, the triangles fill the whole surface and do not overlap. The coordinates of an anchor point at a given depth are computed. The anchor point can be located on a reference surface, for example, the surface on which the subject lies. The anchor point in conjunction with the depth map defines a 3D hull which has a volume. Alternatively, the coordinates of points on an anchor surface corresponding to the set of depths of a reference surface can be computed. The anchor surface in conjunction with the depth map also defines a 3D hull which has a volume. A volume can be computed for each 3D hull obtained from each depth map. A concatenation of all sequential volumes forms a temporal sequence of instantaneous volumes across time intervals during inspiration and expiration. The signal can be de-trended to remove low frequency variations and smoothed using a Fast Fourier Transform (FFT) or a filter. Additionally, the volumetric data can be calibrated so as to convert device-dependent volume data into device-independent data, for example in L, mL, or $cm^3$. A mapping or function that performs such conversion is deemed a calibration function. These functions can be estimated, for example by performing regression or fitting of volumetric data measured via the procedure described above to volumetric data obtained with spirometers. It should be appreciated that, in environments where the patient is free to move around while being monitored for respiratory function, it may be necessary to build perspective-dependent calibration functions specific to the device from which the depth maps are being derived. Data capture from different points of view can be performed and perspective-dependent volume signals derived. Processing from each point of view will lead to perspective-dependent volume signals from which multiple calibration tables can be constructed. Calibration for various perspectives intermediate to those tested can be accomplished via interpolation.

A "segment of a breathing signal" refers to some or all of the subject's breathing signal. A segment can be, for instance, one or more dominant cycles of the subject's breathing signal or a fraction or multiple fractions of one dominant cycle of the subject's breathing signal. The dominant cycle may be selected in many ways; for example by extracting any one breathing cycle from the chosen segment, by averaging all the breathing cycles in a signal, by extracting the cycle with the smallest or largest period, among others. A signal segment may comprise a phase-shifted portion of the subject's breathing signal. Methods for obtaining a segment of a signal are well established in the signal processing arts. A segment of the subject's breathing signal is used herein for comparison purposes such that a breathing pattern for the subject can be identified.

"Identifying a breathing pattern" for the subject comprises visual inspection of the breathing pattern and then comparing that pattern to one or more known reference patterns and selecting a reference pattern that is a closest visual match.

A "breathing pattern" refers to a movement of the target region due to the flow of air over a period of inspiration and expiration. The breathing pattern may be any of: Eupnea, Bradypnea, Tachypnea, Hypopnea, Apnea, Kussmaul, Cheyne-Stokes, Biot's, Ataxic, Apneustic, Agonal, or Thoracoabdominal, as are generally understood by medical doctors, nurses, pulmonologists, respiratory therapists, among others. The identified breathing pattern for the subject can then be used by trained practitioners to determine any of: pulmonary fibrosis, pneumothorax, Infant Respiratory Distress Syndrome, asthma, bronchitis, or emphysema.

A "remote sensing environment" refers to non-contact, non-invasive sensing, i.e., the sensing device does not physically contact the subject being sensed. The sensing device can be any distance away from the subject, for example, as close as less than an inch to as far as miles in the case of telemedicine which is enabled by remote communication. The environment may be any settings such as, for example, a hospital, ambulance, medical office, and the like.

Example Image-Based System

Figure 4:
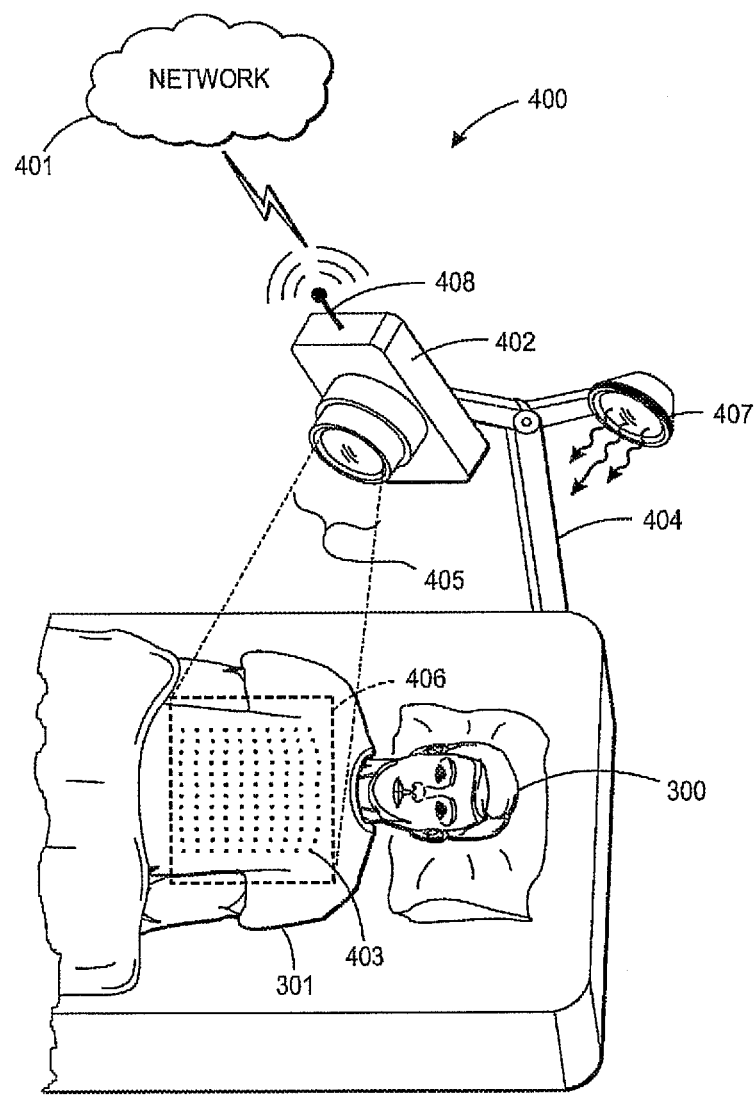
FIG. 4 illustrates one embodiment of an example image-based depth sensing device acquiring video images of the target region of the subject of FIG. 3 being monitored for respiratory function assessment.

Reference is now being made to FIG. 4 which illustrates one embodiment of an example image-based depth sensing device acquiring video images of the target region of the subject of FIG. 3 being monitored for respiratory function assessment. In this embodiment, the image-based depth sensing device used to obtain video images of the subject's target region from which the time-varying sequence of depth maps is obtained can be, for example, a red green blue depth (RGBD) camera, an infrared depth camera, a passive stereo camera, an active stereo camera, an array of cameras, or a 2D monocular video camera. In another embodiment where a non-image-based depth sensing device is used to acquire depth measurement data from which the time-varying sequence of depth maps is obtained can be, for example, a LADAR device, a LiDAR device, a photo wave device, or a time-of-flight measurement device.

Examination room 400 has an example image-based depth sensing device 402 to obtain video images of a subject 301 shown resting his/her head on a pillow while his/her body is partially covered by sheet. Subject 301 is being monitored for respiratory function assessment. Patient 301 is wearing a shirt 301 shown with a patterned array of reflective marks, individually at 403. It is to be noted that clothing with patterned array of reflective marks is not needed when patterns are projected by the illumination source system. Video camera 402 is rotatably fixed to support arm 404 such that the camera's field of view 405 can be directed by a technician onto target region 406. Support arm 404 is mounted on a set of wheels (not shown) so that video acquisition system 402 can be moved from bed to bed and room to room. Although patient 300 is shown in a prone position lying in a bed, it should be appreciated that video of the target region 406 can be captured while the subject is positioned in other supporting devices such as, for example, a chair or in a standing position. Video camera 402 comprises imaging sensors arrayed on a detector grid. The sensors of the video camera are at least sensitive to a wavelength of illumination source system 407 being reflected by the reflective marks 403. The illumination source system may be any light wavelength that is detectable by sensors on the camera's detector array. The illumination sources may be manipulated as needed and may be invisible to the human visual system. The illumination source system may be arranged such that it may project invisible/visible patterns of light on the subject.

A central processor integral to the video camera 402 and in communication with a memory (not shown) functions to execute machine readable program instructions which process the video to obtain the time-varying sequence of depth maps. The obtained sequence of depth maps may be wirelessly communicated via transmission element 408 over network 401 to a remote device operated by, for instance, a nurse, doctor, or technician for further processing, as needed, and for respiratory function assessment of patient 300. Alternatively, the captured video images are wirelessly communicated over network 401 via antenna 408 to a remote device such as a workstation where the transmitted video signal is processed to obtain the time-varying sequence of depth maps. The depth maps are, in turn, processed to obtain the time-varying breathing signal. Camera system 402 may further include wireless and wired elements and may be connected to a variety of devices via other means such as coaxial cable, radio frequency, Bluetooth, or any other manner for communicating video signals, data, and results. Network 401 is shown as an amorphous cloud wherein data is transferred in the form of signals which may be, for example, electronic, electromagnetic, optical, light, or other signals. These signals may be communicated to a server which transmits and receives data by means of a wire, cable, fiber optic, phone line, cellular link, RF, satellite, or other medium or communications pathway or protocol. Techniques for placing devices in networked communication are well established. As such, further discussion as to specific networking techniques is omitted herein.

Flow Diagram of One Embodiment

Figure 5:
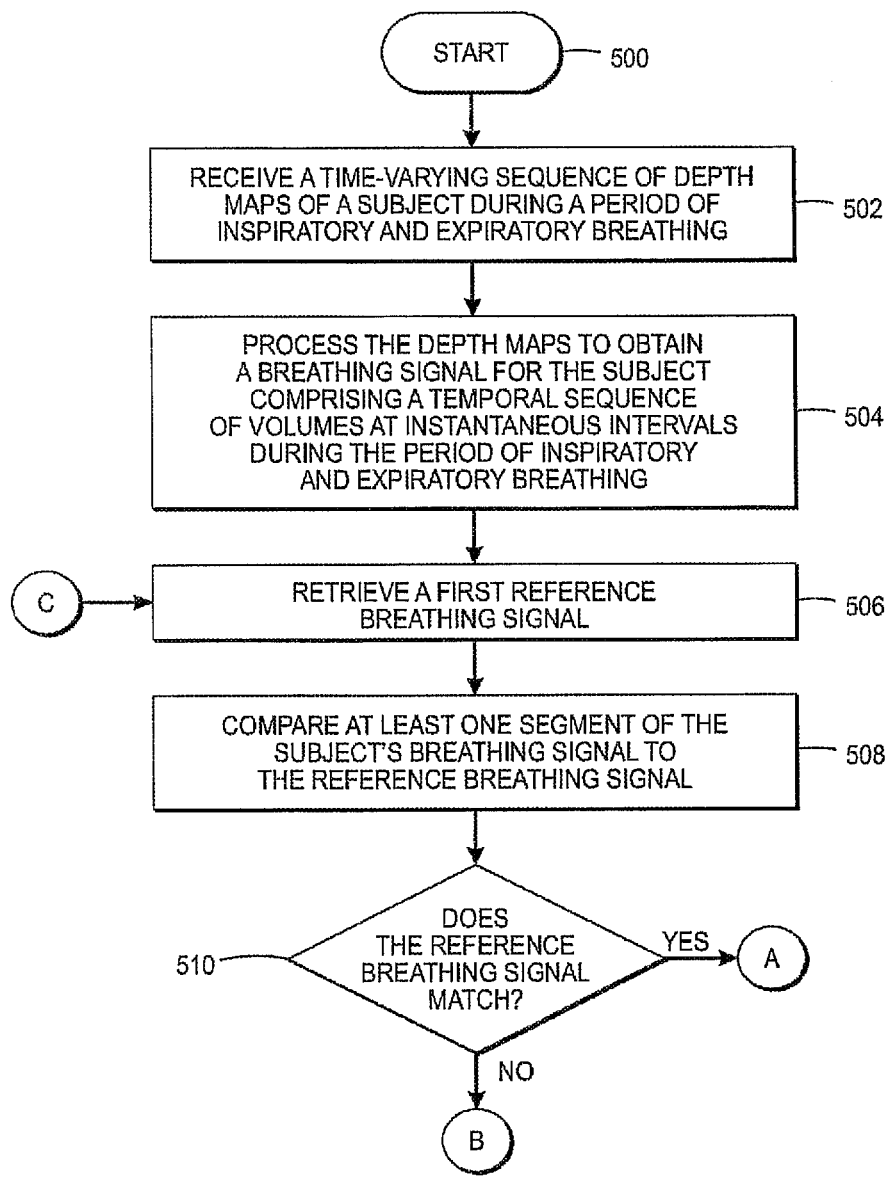
FIG. 5 is a flow diagram which illustrates one example embodiment of the present method for identifying a breathing pattern of a subject for respiratory function assessment in a remote sensing environment.

Reference is now being made to the flow diagram of FIG. 5 which illustrates one embodiment of the present method for identifying a breathing pattern of a subject for respiratory function assessment in a remote sensing environment. Flow begins at 500 and immediately proceeds to step 502.

At step 502, receive a time-varying sequence of depth maps of a target region of a subject of interest being monitored for breathing pattern identification. The depth maps are of the target region over a period of inspiration and expiration. The target region may be, for example, the subject's anterior thoracic region, a region of the subject's dorsal body, and a side view containing the subject's thoracic region. The depth sensing device may be an image-based depth sensing device or a non-image-based depth sensing device. Various example target regions are shown in FIG. 1.

At step 504, process the depth maps to obtain a breathing signal for the subject comprising a temporal sequence of volumes at instantaneous intervals across time intervals during inspiratory and expiratory breathing. The inspiration may be a maximal forced inspiration and the expiration a maximal forced expiration, or the inspiration and expiration are tidal breathing.

At step 506, retrieve a first reference breathing signal. The reference breathing signals can be retrieved from, for example, a database of reference signals or from a storage device. The reference breathing signal can be received or otherwise obtained from a remote device over a wired or wireless network. Associated with each of the reference breathing signals is a breathing pattern.

At step 508, compare at least one segment of the subject's breathing signal against the retrieved reference breathing signal.

At step 510, a determination is made whether, as a result of the comparison in step 508, the reference signal is a match. If so then processing proceeds with respect to node A of FIG. 6 which is a continuation of the flow diagram of FIG. 5. If, as a result of the comparison performed in step 510 it is determined that the reference breathing signal matches the signal segments) of the subject's breathing signal then flow continues with respect to step 512 wherein the breathing pattern associated with the matching reference signal is determined to be the breathing pattern of the subject.

At step 514, the identified breathing is used for respiratory function assessment of the subject. In this embodiment, further flow stops. In another embodiment, the identified breathing pattern is processed by an artificial intelligence algorithm to determine whether an alert condition exists. If so, then an alert signal is automatically sent using, for example, transmissive element 408 of FIG. 4. The alert signal may comprise, for example, a light blinking, an alarm or a message flashing on a monitor display. Such a notification can take the form of a text message sent to a cellphone of a medical practitioner such as a nurse, pulmonologist, doctor or respiratory therapist. The notification alert may be a pre-recorded voice, text, direct phone call, or video message. Such an alert or notification can take any of a variety of forms and would depend on the particular environment wherein the teachings hereof find their intended uses.

If, as a result of the comparison performed in step 510, it is determined that the reference breathing signal does not match the signal segment(s) of the subject breathing signal then flow continues with respect to node B wherein, at step 516, a determination is made whether more reference breathing signals remain to be obtained for comparison purposes. If so then flow repeats with respect to node C of FIG. 5 wherein, at step 506, a next reference breathing signal is retrieved or is otherwise received or obtained and this next reference breathing signal is then compared to one or more segments of the subject's breathing signal. Otherwise, in this embodiment, further flow stops.

It should be understood that the flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims. All or portions of the flow diagrams may be implemented partially or fully in hardware in conjunction with machine executable instructions.

Example Networked System

Figure 6:
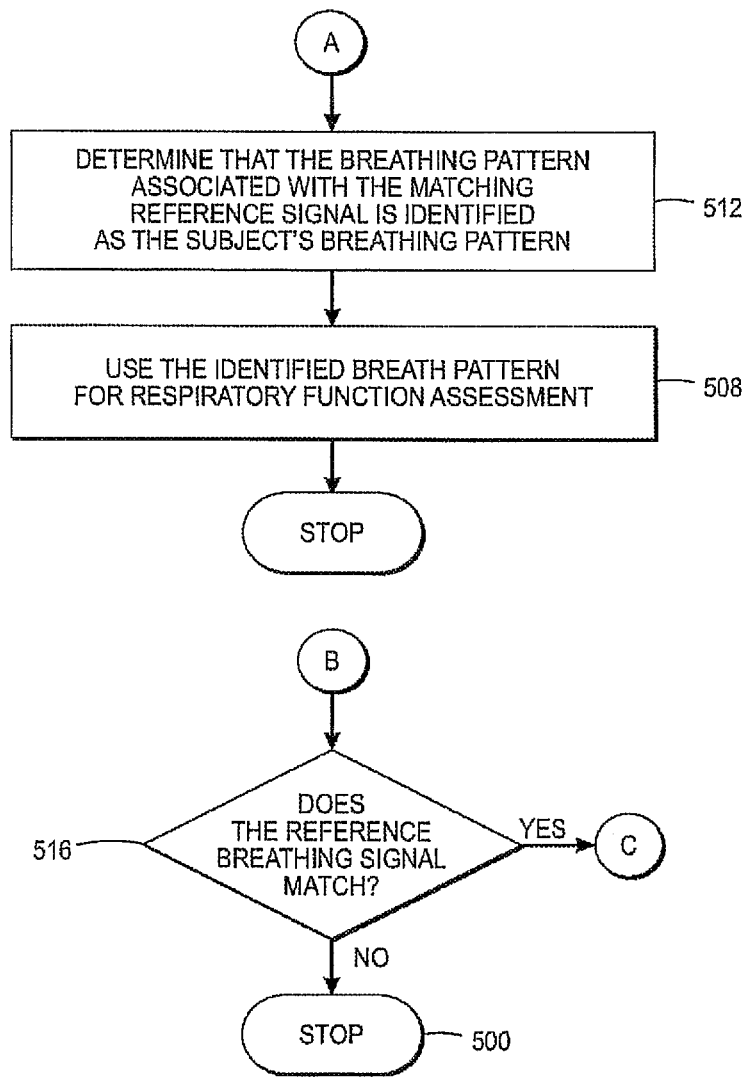
FIG. 6 is a continuation of the flow diagram of FIG. 5 with flow continuing with respect to nodes A or B.
Figure 7:
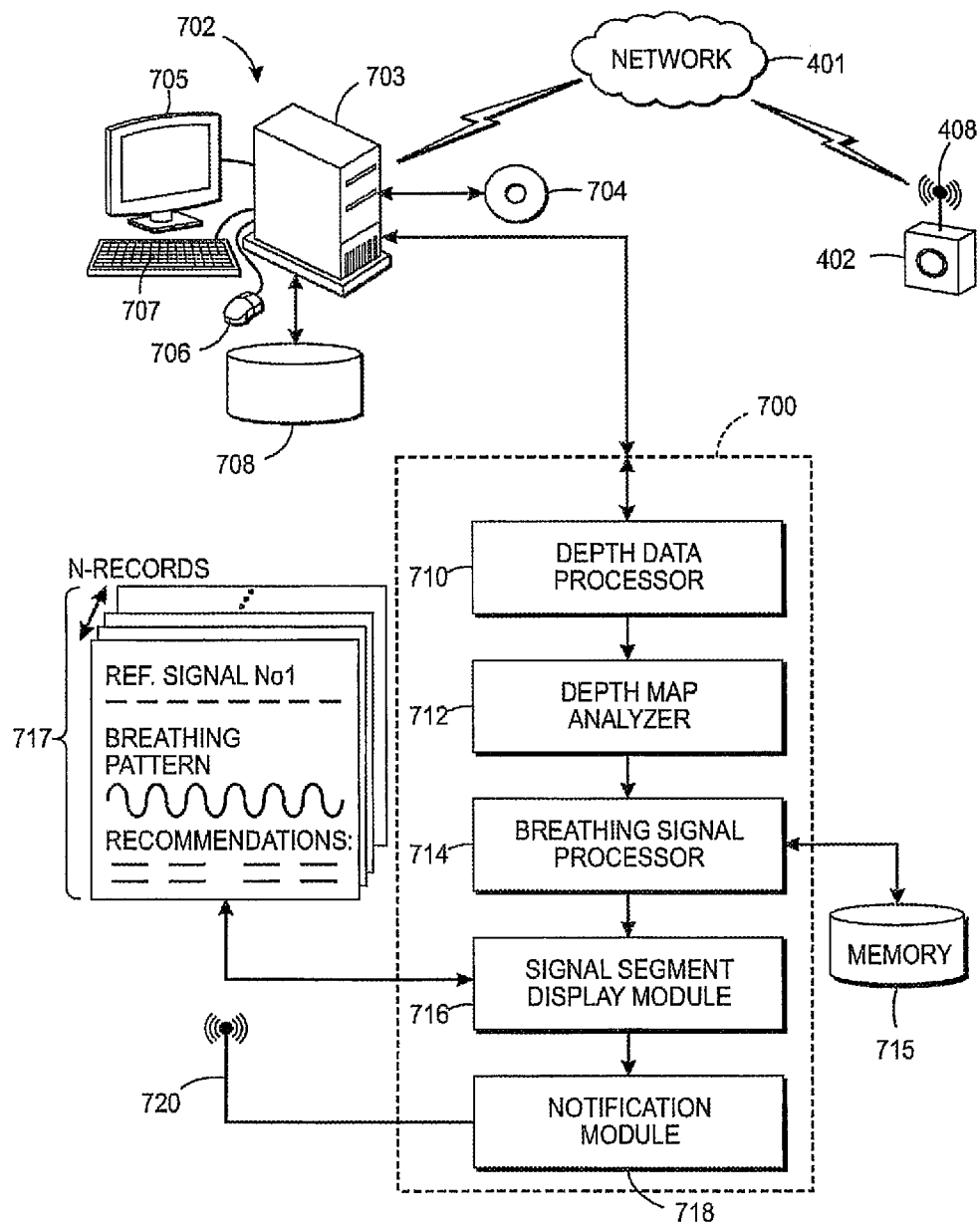
FIG. 7 is a functional block diagram of an example networked system for implementing various aspects of the present method described with respect to the flow diagrams of FIGS. 5 and 6.

Reference is now being made to FIG. 7 which shows a functional block diagram of an example networked system for implementing various aspects of the present method described with respect to the flow diagrams of FIGS. 5 and 6. The system 700 of FIG. 7 illustrates a plurality of modules, processors, and components placed in networked communication with a workstation 702 wherein depth measurement data in the form of a video signal or depth values is transmitted over network 401 via transmissive element 408 by depth sensing device 402 are received for processing.

Workstation 702 includes a hard drive (internal to computer housing 703) which reads/writes to a computer readable media 704 such as a floppy disk, optical disk, CD-ROM, DVD, magnetic tape, etc. Case 703 houses a motherboard with a processor and memory, a communications link such as a network card, graphics card, and the like, and other software and hardware to perform the functionality of a computing device as is generally known in the arts. The workstation includes a graphical user interface which, in various embodiments, comprises display 705 such as a CRT, LCD, touch screen, etc., a mouse 706 and keyboard 707. Information may be entered by a user of the present system using the graphical user interface. It should be appreciated that workstation 702 has an operating system and other specialized software configured to display a wide variety of numeric values, text, scroll bars, pull-down menus with user selectable options, and the like, for entering, selecting, or modifying information displayed on display 705. The embodiment shown is only illustrative. Although shown as a desktop computer, it should be appreciated that computer 702 can be any of a laptop, mainframe, client/server, or a special purpose computer such as an ASIC, circuit board, dedicated processor, or the like. Any of the Information obtained from any of the modules of system 700 including various characteristics of any of the depth sensors can be saved to storage device 708.

In the system 500, Depth Data Processor 710 processes the acquired data to obtain a time-varying sequence of depths maps of the target region over a period of inspiration and expiration. Depth Map Analyzer 712 receives the time-varying sequence of depth maps from Processor 710 and proceeds to process the received depth maps to produce a time-varying breathing signal for the subject being monitored for respiratory function assessment. Breathing Signal Processor 714 receives the time-varying breathing signal and identifies one or more signal segments in the subject's breathing signal that will be used for comparison purposes and may further store the data to Memory 715. Signal Segment Display Module 716 receives the segment(s) of the subject's breathing signal and retrieves one or more records, collectively at 717, containing reference breathing signals and associated breathing patterns which are shown by way of example in a first of n-records which may also contain associated medical conditions and recommendations. The retrieved reference breathing signal segment(s) are displayed for the practitioner so that a matching reference breathing signal can be selected. The breathing pattern associated with the selected reference breathing signal is determined to be a match for the subject's breathing pattern. In this embodiment, Notification Module 718 implements an artificial intelligence program to determine whether an alert signal needs to be sent to a nurse, doctor or respiratory therapist via antenna element 720. Such an alert or notification can take any of a variety of forms. Notification Module 718 may further communicate any of the values, data, diagrams, results generated by any of the modules of system 700 to a remote device.

It should be understood that any of the modules and processing units of FIG. 7 are in communication with workstation 702 via pathways (not shown) and may further be in communication with one or more remote devices over network 401. Further, the workstation and any remote devices may further read/write to any of the records 716 which may be stored in a database, memory, or storage device (not shown). Any of the modules may communicate with storage devices 708 and memory 715 via pathways shown and not shown and may store/retrieve data, parameter values, functions, records, and machine readable/executable program instructions required to perform their intended functions. Some or all of the functionality for any of the modules of the functional block diagram of FIG. 7 may be performed, in whole or in part, by components internal to workstation 702 or by a special purpose computer system.

Various modules may designate one or more components which may, in turn, comprise software and/or hardware designed to perform the intended function. A plurality of modules may collectively perform a single function. Each module may have a specialized processor and memory capable of executing machine readable program instructions. A module may comprise a single piece of hardware such as an ASIC, electronic circuit, or special purpose processor. A plurality of modules may be executed by either a single special purpose computer system or a plurality of special purpose systems operating in parallel. Connections between modules include both physical and logical connections. Modules may further include one or more software/hardware components which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network.

Example Breathing Patterns

Figure 8:
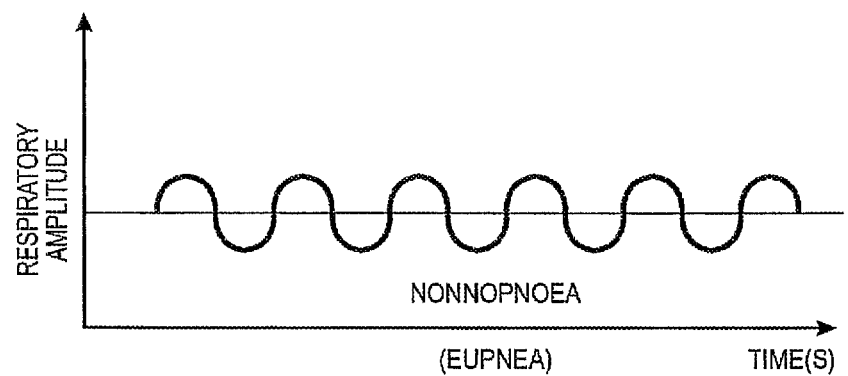
FIG. 8 shows an example breathing pattern associated with normal breathing (eupnea) as observed normally under resting conditions.

FIG. 8 shows an example breathing pattern associated with normal breathing (Eupnea) as observed normally under resting conditions.

Figure 9:
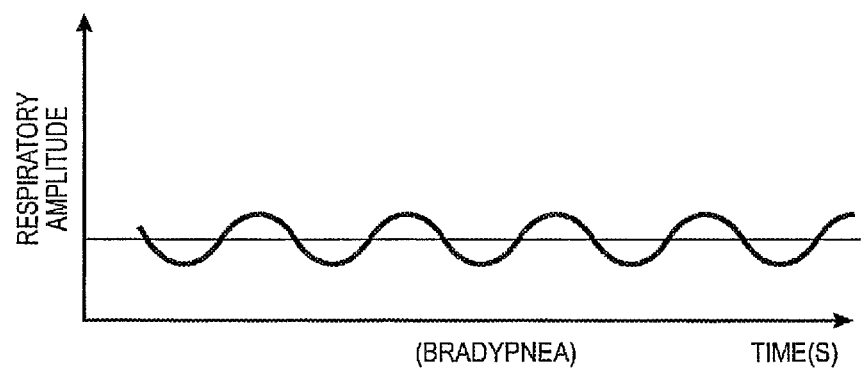
FIG. 9 shows an example Bradypnea breathing pattern characterized by an unusually slow rate of breathing.

FIG. 9 shows an example Bradypnea breathing pattern which is characterized by an unusually slow rate of breathing. Bradypnea is typically characterized by a period of respiration less than 12 breaths per minute (bpm) for patients in the range of between 12 and 50 years of age. Rates of breathing differ for older adults as well as younger patients. If an individual has this type of breathing, it can mean that the individual is not receiving a proper amount of oxygen.

Figure 10:
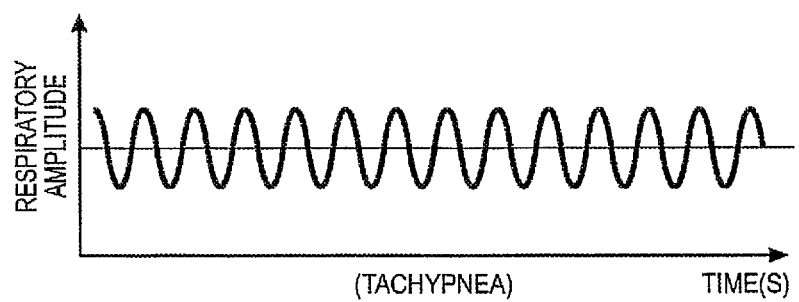
FIG. 10 shows an example Tachypnea breathing pattern characterized as an unusually fast respiratory rate.

FIG. 10 shows an example Tachypnea breathing pattern characterized by an unusually fast respiratory rate typically greater than 20 breaths per minute (bpm). Tachypnea can be associated with high fever when the body attempts to rid itself of excess heat. The rate of respiration increases at a ratio of about eight breaths per minute for every degree Celsius above normal. Other causes include pneumonia, compensatory respiratory alkalosis as the body tries to expel excess carbon dioxide, respiratory insufficiency, lesions in the respiratory control center of the brain, and poisoning. Tachypnea of a newborn is an elevation of the respiratory rate which can be due to fetal lung water.

Figure 11:
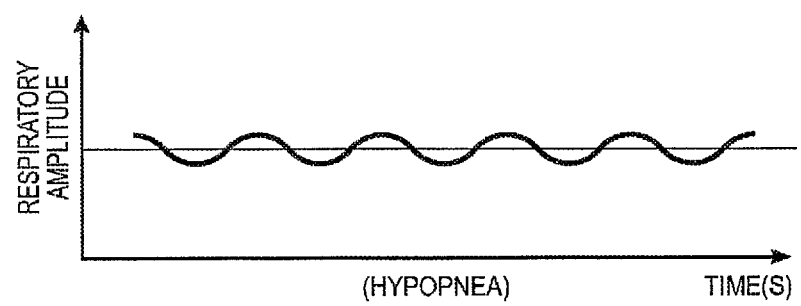
FIG. 11 shows an example Hypopnea breathing pattern characterized by an abnormally shallow and slow respiration rate.

FIG. 11 shows an example Hypopnea breathing pattern characterized by an abnormally shallow and slow respiration rate. Hypopnea typically occurs with advanced age. In well-conditioned athletes, it may be appropriate and is often accompanied by a slow pulse. Otherwise, it is apparent when pleuritic pain limits excursion and is characteristic of damage to the brainstem. Hypopnea accompanied by a rapid, weak pulse, may mean a brain injury.

Figure 12:
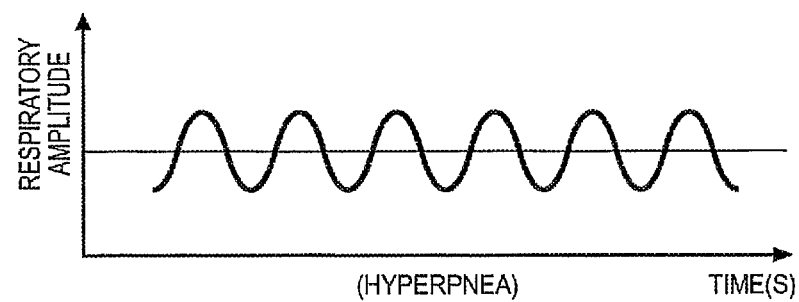
FIG. 12 shows an example Hyperpnea breathing pattern characterized by an exaggerated deep, rapid, or labored respiration.

FIG. 12 shows an example Hyperpnea breathing pattern characterized by an exaggerated deep, rapid, or labored respiration. It occurs normally with exercise and abnormally with aspirin overdose, pain, fever, hysteria, or a condition in which the supply of oxygen is inadequate. Hyperpnea may indicate cardiac disease and respiratory disease. Also spelled hyperpnoea.

Figure 13:
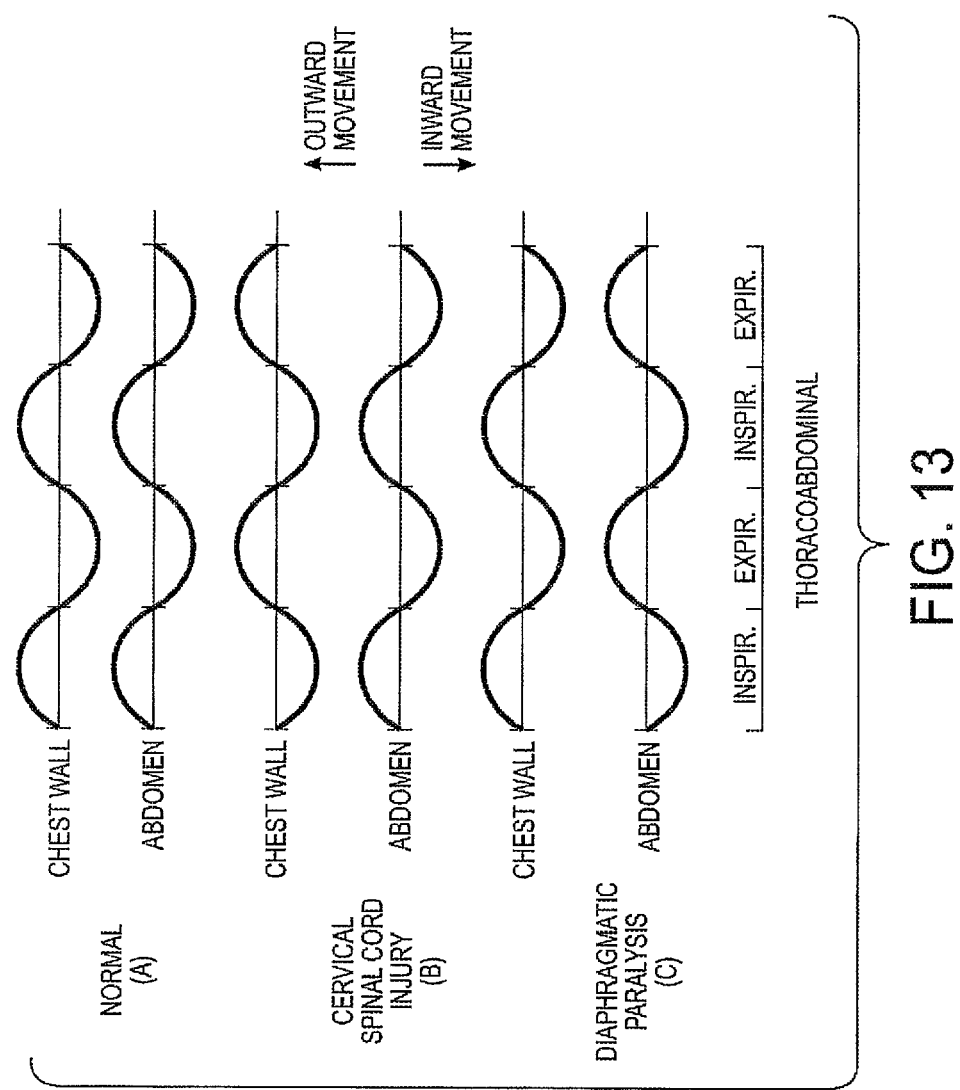
FIG. 13 shows an example Thoracoabdominal breathing pattern that involves trunk musculature to "suck" air into the lungs for pulmonary ventilation.

FIG. 13 shows an example Thoracoabdominal breathing that involves trunk musculature to "suck" air into the lungs for pulmonary ventilation. This is typical in reptiles and birds. In humans, it can indicate a neuromuscular disorder such as a cervical spinal injury or a diaphragmatic paralysis.

Figure 14:
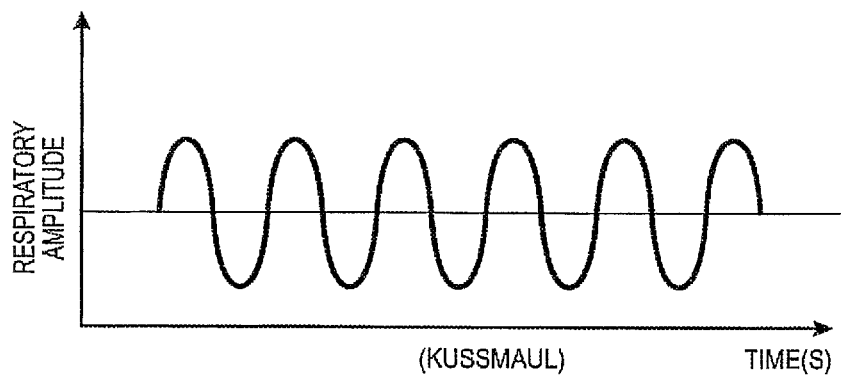
FIG. 14 shows an example Kussmaul breathing pattern characterized by rapid, deep breathing due to a stimulation of the respiratory center of the brain triggered by a drop in pH.

FIG. 14 shows an example Kussmaul breathing pattern characterized by rapid, deep breathing due to a stimulation of the respiratory center of the brain triggered by a drop in pH. Kussmaul breathing is normal during exercise but is often seen in patients with metabolic acidosis.

Apnea (not shown) is a cessation of breathing for an extended period such as 20 seconds or more, typically during sleep. Apnea is divided into three categories: (1) obstructive, resulting from obstruction of the upper airways; (2) central, caused by some pathology in the brain's respiratory control center; and (3) mixed, a combination of the two.

In one embodiment, the flow diagram of FIG. 5 may be slightly modified to detect that a subject is having an apnea episode. For example, a time-varying sequence of depth maps of a target region of a subject of interest may be received. However, rather than obtaining the first reference breathing signal to compare against at least one segment of the subject's breathing signal, the time-varying sequence of depth maps may be continuously analyzed to determine a time duration of each time period when a change in the time-varying sequence of depth maps is at a minimum. In one embodiment, the continuous analysis of the time-varying sequence of depth maps may be similar to obtaining the "subject's breathing signal" as defined above.

The subject's breathing signal may be graphically illustrated. For example, the change in the time-varying sequence of depth maps being at a minimum may be illustrated graphically as a flat line on a breathing pattern chart. For example, in FIGS. 15 and 16 periods of apnea are illustrated as a time period when no change occurs in the breathing pattern.

In one embodiment, apnea may be detected when the time-varying sequence of depth maps are analyzed. The analyzing may include comparing one or more depth maps in the time-varying sequence of depth maps to another depth map within the time-varying sequence; when the comparison indicates no change, or a minimal change (e.g., a measure of a change in instantaneous volume or shape smaller than a minimum threshold) in the depth of the target region, apnea may be detected. In one embodiment, the one or more depth maps in the time-varying sequence of depth maps may be temporally consecutive depth maps (e.g., each one of ten or more consecutive depth maps n, n+1, . . . , n+9, where n is a discrete temporal index, are analyzed, typically in a pair wise manner). In another embodiment, the one or more depth maps in the time-varying sequence of depth maps may be non-consecutive depth maps (e.g., for ten consecutive depth maps, depth maps n and n+2 may be analyzed, then depth maps n+2 and n+4, may be analyzed and so forth; more generally, for positive integers k and m, frames n, n+m, n+2m, . . . , n+km may be analyzed, typically in a pair wise manner). In yet another embodiment, non-consecutive groups of consecutive depth maps in the sequence of depth maps may be analyzed (e.g., every consecutive pair in a group of ten consecutive depth maps, then no analysis is performed for a group of five consecutive depth maps, then every consecutive pair in a group of ten consecutive depth maps, and so forth). Combinations of these embodiments are also possible.

The next depth maps in the time-varying sequence of depth maps are compared and the comparison indicates no change, or a minimal change in the depth of the target region. When no change or a minimal change is detected for the time-varying sequence of depth maps for a pre-defined time period (e.g., 20 second or more), the subject may be determined to be having an apnea episode.

In one embodiment, the analysis of depth maps may include extracting instantaneous volumes from each of the depth maps being analyzed in the depth map sequence, and the comparison may include computing differences in the extracted instantaneous volumes. Instantaneous volumes are obtained from processing the depth maps. In one embodiment, the depth map comprises a 3D hull defined by a set of 3D coordinates namely their horizontal, vertical and depth coordinates (x, y and z respectively). Points in the hull can be used to form a tessellation of the target area. The tessellation can be uniform and can be comprised of triangles, squares, rectangles and other polygons, or it could also be non-uniform and be comprised of different types of geometric shapes. By definition of a tessellation, the geometric shapes fill the whole surface and do not overlap. The coordinates of an anchor point at a given depth are computed. The anchor point can be located on a reference surface, for example, the surface on which the subject lies. The anchor point in conjunction with the depth map defines a 3D hull which has a volume. Alternatively, the coordinates of points on an anchor surface corresponding to the set of depths of a reference surface can be computed. The anchor surface in conjunction with the depth map also defines a 3D hull which has a volume. A volume can be computed for each 3D hull obtained from each depth map.

In another embodiment, the analysis of depth maps may include extracting 3D shape descriptors from each of the depth maps being analyzed in the depth map sequence, and the comparison may include computing differences in shapes as determined by the 3D shape descriptors. 3D shape descriptors usually focus on attributes like surface characteristics, as opposed to attributes such as color and texture, which are better suited for 2D image description. 3D shape descriptors can be broadly classified into feature-based and graph-based. A 3D shape is described by a set of points in the 3D space, each point having a specific three-dimensional coordinate. Describing a shape is achieved by constructing a numeric representation of the mesh formed by the set of points; said representation is usually denoted a signature or descriptor. Computation of similarity between metrics descriptors is tightly related to the 3D descriptor of choice, as similarity/dissimilarity metrics are usually computed in the descriptor space and are always relative to it. Examples of other descriptors that may be used in this embodiment include surface area to volume ratio, compactness (non-dimensional ratio of the volume squared over the cube of the surface area), crinkliness (surface area of the model divided by the surface area of a sphere having the same volume as the model), convex hull features, bounding box aspect ratio, Euler numbers, cord and angle histograms, shape distributions, shape histograms, radial-cosine transforms, shape spectrums, and probability density based descriptors. Other shape descriptors may be used.

In one embodiment, the apnea episode may be detected in real-time. As noted above, the processing of the time-varying sequence of depth maps may occur as the time-varying sequence of depth maps are captured.

Detecting the apnea episode from the processing of the time-varying sequence of depth maps may help provide early detection for other conditions. For example, when the apnea episode is detected in an infant, the infant may be at risk for sudden infant death syndrome (SIDS). In addition, when the apnea episode is detected, the system 700 may initiate an alert signal to a medical professional. The system 700 may also communicate to any of a memory, a storage device, a display device, a handheld device, a handheld cellular device or a remote device over a network (e.g., via the notification module 718) that the subject is having an apnea episode.

Figure 15:
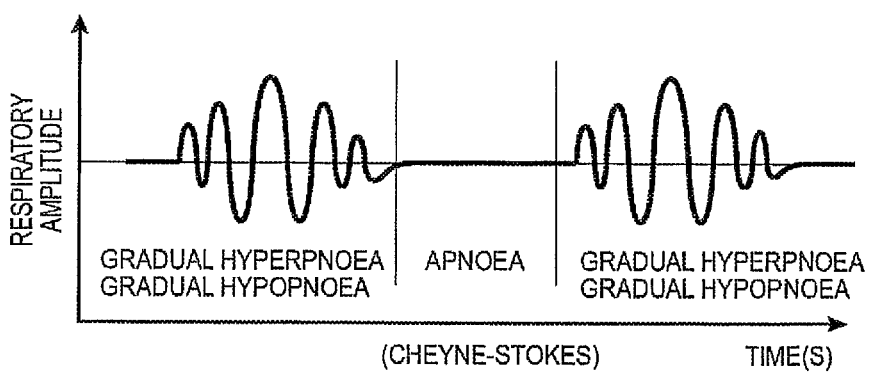
FIG. 15 shows an example Cheyne-Stokes respiration pattern which is characterized by a crescendo-decrescendo pattern of breathing followed by a period of central apnea.

FIG. 15 shows an example Cheyne-Stokes respiration which is characterized by a crescendo-decrescendo pattern of breathing followed by a period of central apnea. This is often seen in conditions like stroke, brain tumor, traumatic brain injury, carbon monoxide poisoning, metabolic encephalopathy, altitude sickness, narcotics use and in non-rapid eye movement sleep of patients with congestive heart failure.

Figure 16:
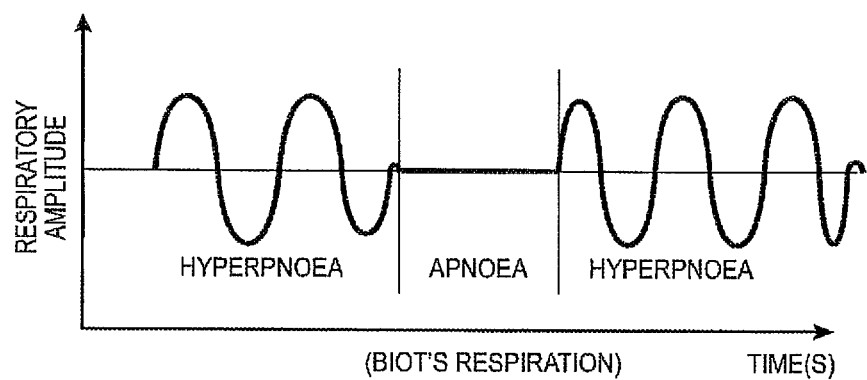
FIG. 16 shows an example Biot's respiration pattern which is characterized by abrupt and irregularly alternating periods of apnea with periods of breathing that are consistent in rate and depth.

FIG. 16 shows an example Biot's respiration which is characterized by abrupt and irregularly alternating periods of apnea with periods of breathing that are consistent in rate and depth. Biot's respiration is indicative of an increased intracranial pressure.

Figure 17:
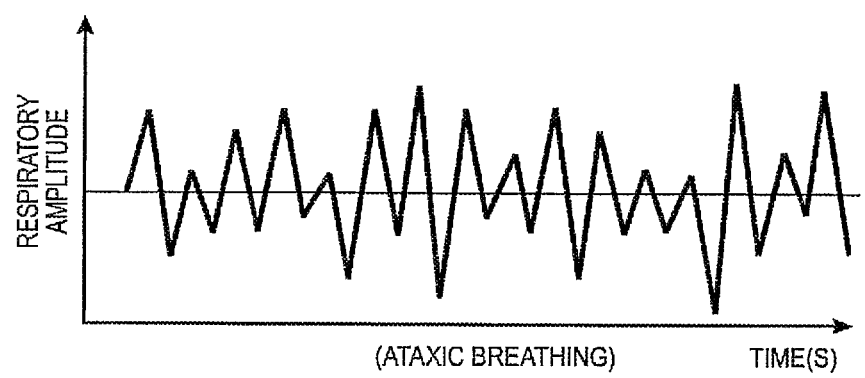
FIG. 17 shows an example Ataxic breathing pattern which is a completely irregular breathing pattern with continually variable rate and depth of breathing.

FIG. 17 shows an example Ataxic breathing pattern which is a completely irregular breathing pattern with continually variable rate and depth of breathing. Ataxis is indicative of lesions in the respiratory centers in the brainstem.

Figure 18:
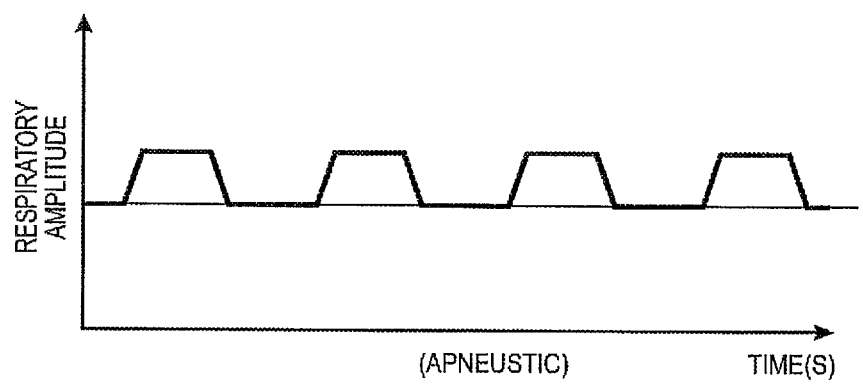
FIG. 18 shows an example Apneustic breathing pattern which is characterized by a prolonged inspiratory phase followed by expiration apnea.

FIG. 18 shows an example Apneustic breathing pattern which is characterized by a prolonged inspiratory phase followed by expiration apnea. The rate of Apneustic breathing is usually around 1.5 breaths per minute (bpm). An Apneustic breathing pattern is often associated with head injury.

Figure 19:
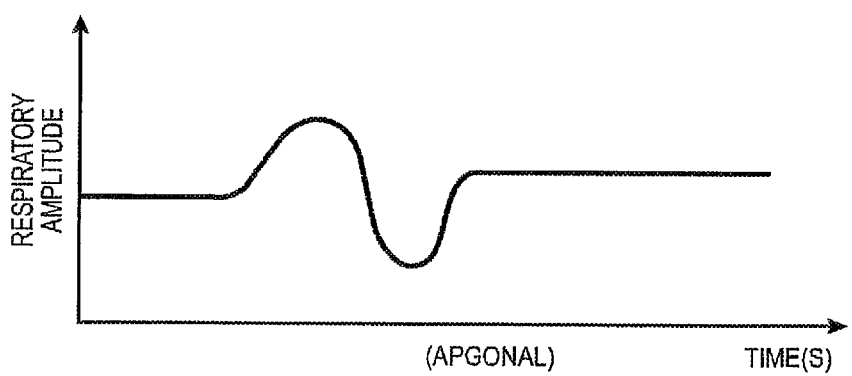
FIG. 19 shows an example Agonal breathing which is abnormally shallow breathing pattern often related to cardiac arrest.

FIG. 19 shows example Agonal breathing which is abnormally shallow breathing pattern often related to cardiac arrest.

Performance Results

Figure 20:
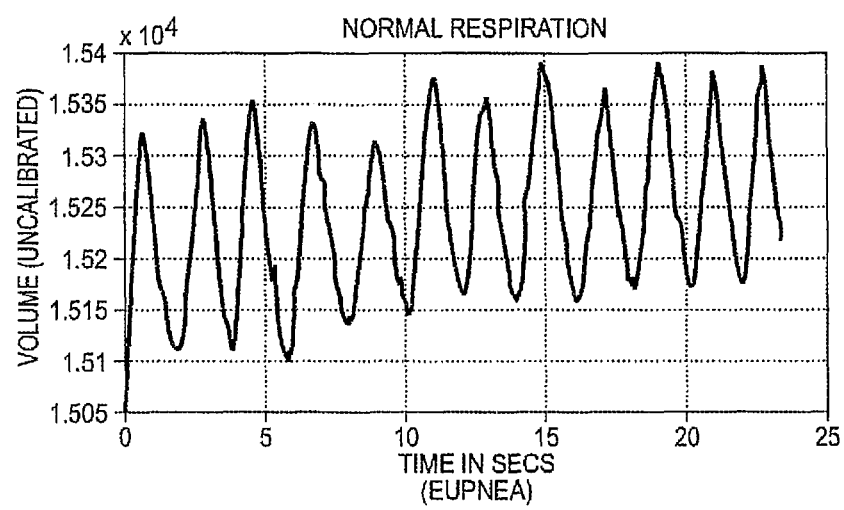
FIG. 20 shows a normal respiration pattern measured via the use of a depth sensing device with the depth maps being processed in accordance with the teachings hereof.
Figure 21:
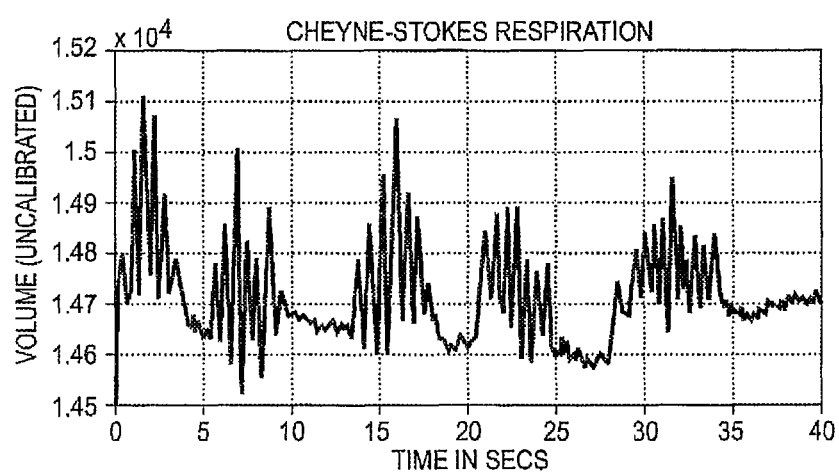
FIG. 21 shows a test subject's Cheyne-Stokes breathing pattern measured using the techniques disclosed herein.
Figure 22:
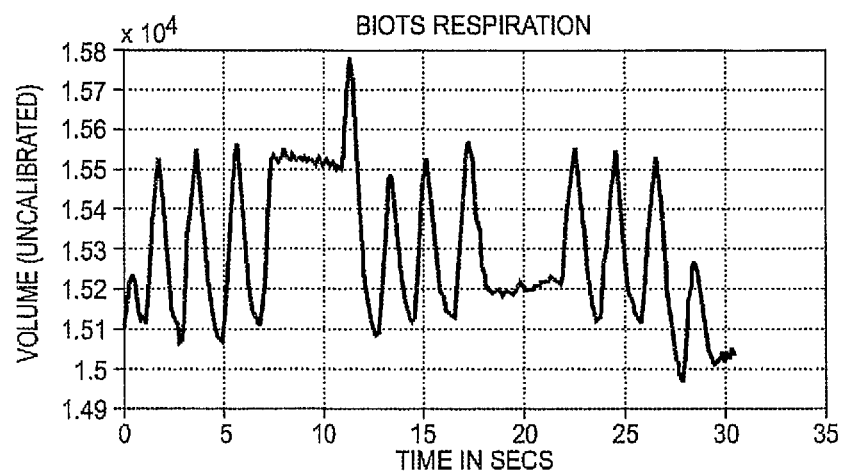
FIG. 22 shows a test subject's Biot's pattern measured using the techniques disclosed herein.
Figure 23:
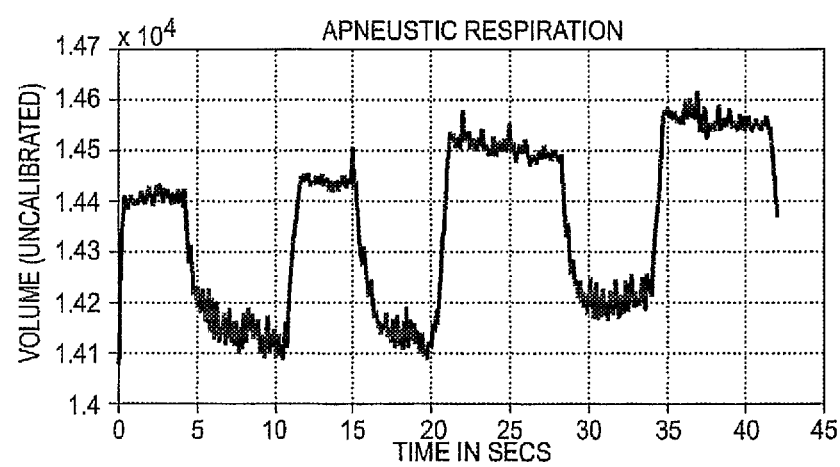
FIG. 23 shows a test subject's Apneustic pattern measured using the present methods.
Figure 24:
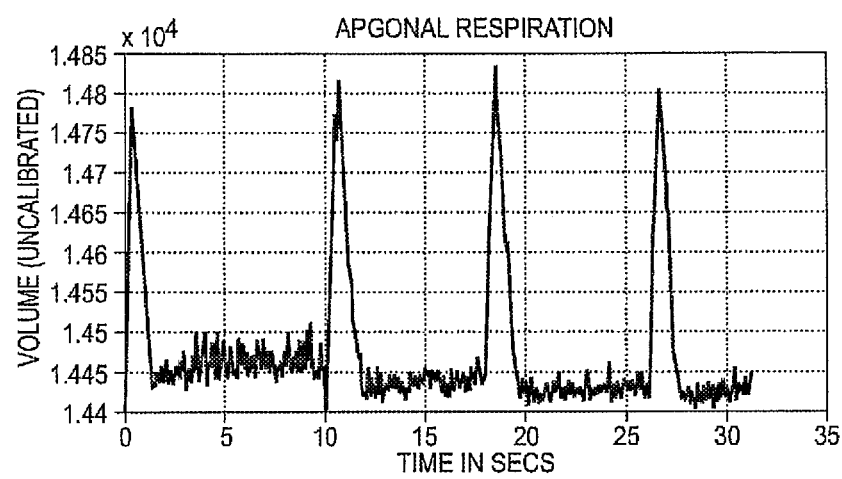
FIG. 24 shows a test subject's Agonal breathing pattern measured using the present methods.

A person with training in respiratory diseases emulated various breathing patterns for our tests using an active-stereo-based system to acquire a time-series signal used to generate depth maps. Depth data was captured at 30 fps. The signals were processed in accordance with the teachings hereof and the resulting breathing patterns plotted for comparison purposes. FIG. 20 shows a normal respiration pattern captured using a depth sensing device with the depth maps being processed in accordance with the teachings hereof which matches well with the normal breathing pattern of FIG. 8. FIG. 21 shows an example Cheyne-Stokes breathing pattern generated using the techniques disclosed herein. Compared this to the Cheyne-Stokes pattern of FIG. 15. FIGS. 22, 23 and 24 shows, respectively, a Biot's pattern, an Apneustic pattern, and an Agonal pattern generated using the present methods. Compare these to the Biot's pattern of FIG. 16, the Apneustic pattern of FIG. 18 and the Agonal pattern of FIG. 19. As can be seen by an examination of the results, an experienced pulmonologist would be able to classify the breathing patterns generated using the teachings disclosed herein, and therefrom identify associated medical reasons for respiratory function assessment.

Various Embodiments

The teachings hereof can be implemented in hardware or software using any known or later developed systems, structures, devices, and/or software by those skilled in the applicable art without undue experimentation from the functional description provided herein with a general knowledge of the relevant arts. One or more aspects of the methods described herein are intended to be incorporated in an article of manufacture, including one or more computer program products, having computer usable or machine readable media. The article of manufacture may be included on at least one storage device readable by a machine architecture embodying executable program instructions capable of performing the methodology and functionality described herein. Additionally, the article of manufacture may be included as part of a complete system or provided separately, either alone or as various components. It will be appreciated that various features and functions, or alternatives thereof, may be desirably combined into other different systems or applications. Presently unforeseen or unanticipated alternatives, modifications, variations, or improvements therein may become apparent and/or subsequently made by those skilled in the art, which are also intended to be encompassed with the scope of the following claims.

Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining that a subject is having an apnea episode, comprising:
    capturing images of the subject while illuminated by a projected pattern of structured light, wherein the projected pattern of structured light is emitted by light emitting diodes arrayed in a uniform pattern fixed to an item of clothing worn by the subject;
    generating a time-varying sequence of depth maps from the images based upon a comparison of spatial characteristics of reflections of the projected pattern of structured light in conjunction with a known distance between a light projector that projects the projected pattern of structured light and a camera that captures the images and characterized distortions at different locations to calculate a depth map for each one of the images;

receiving the time-varying sequence of depth maps obtained for a target region of the subject;
the use of a processor, the processor performing the operations of:
continuously analyzing the time-varying sequence of depth maps to determine a time duration of each time period when a change in the time-varying sequence of depth maps is at a minimum, wherein the continuously analyzing comprises extracting a volume from each one of the time-varying sequence of depth maps based on a tessellation of a target area of the subject formed by points in a three dimensional hull defined by three dimensional coordinates, wherein the tessellation comprises uniform or non-uniform geometric shapes that fill an entire surface of the three dimensional hull and do not overlap and computing differences in the volume extracted from the each one of the time-varying sequence of depth maps, wherein the differences in the volume is used to determine the time duration when the change in the time-varying sequence of depth maps is at the minimum;
determining that the subject is having the apnea episode in response to the time duration being at least a pre-defined length of time; and
sending a text message to a cellphone of a medical practitioner in response to the determining that the subject is having the apnea episode.

2. The method of claim 1, wherein the target region of the subject comprises at least one of: an anterior thoracic region, a region of a dorsal body, a side view containing a thoracic region, or a view with a sheet covering a body of the subject.

3. The method of claim 1, wherein the camera comprises an image-based depth sensing device comprising any of: a red green blue depth (RGBD) camera, an infrared depth camera, a passive stereo camera, an array of cameras, an active stereo camera, or a monocular video camera.

4. The method of claim 1, wherein the camera comprises any of: a red green blue (RGB) camera, an infrared camera, a multispectral camera, or a hyperspectral camera.

5. The method of claim 1, wherein, in response to the subject being an infant, determining that the subject is at risk for sudden infant death syndrome.

6. The method of claim 1, wherein, in response to the subject having the apnea episode, performing any of: initiating an alert, or signaling a medical professional.

7. The method of claim 1, further comprising:
communicating to any of: a memory, a storage device, a display device, a handheld wireless device, a handheld cellular device, or a remote device over a network that the subject is having the apnea episode.

8. The method of claim 1, wherein the pre-defined length of time is at least 20 seconds.

9. The method of claim 1, wherein the determining that the subject is having the apnea episode occurs in real-time.

10. The method of claim 1, wherein the analyzing further comprises:
extracting shape descriptors from each of the time-varying sequence of depth maps, the shape descriptors being used for comparison purposes to determine the time duration when a change in shape is at a minimum.

11. A system for determining that a subject is having an apnea episode, comprising:
an array of light emitting diodes in a uniform pattern fixed to an item of clothing worn by the subject to project a pattern of structured light;
a camera to capture images of the subject while illuminated by the pattern of structured light and to generate a time-varying sequence of depth maps from the images based upon a comparison of spatial characteristics of reflections of the pattern of structured light in conjunction with a known distance between the light projector and the camera that captures the images and characterized distortions at different locations to calculate a depth map for each one of the images; and
a work station in communication with the camera over a network, the work station comprising:
a processor; and
a memory storing machine readable program instructions, which when executed by the processor cause the processor to perform operations, the operations comprising:
receiving the time-varying sequence of depth maps obtained for a target region of the subject;
continuously analyzing the time-varying sequence of depth maps to determine a time duration of each time period when a change in the time-varying sequence of depth maps is at a minimum, wherein the continuously analyzing comprises extracting a volume from each one of the time-varying sequence of depth maps based on a tessellation of a target area of the subject formed by points in a three dimensional hull defined by three dimensional coordinates, wherein the tessellation comprises uniform or non-uniform geometric shapes that fill an entire surface of the three dimensional hull and do not overlap and computing differences in the volume extracted from the each one of the time-varying sequence of depth maps, wherein the differences in the volume is used to determine the time duration when the change in the time-varying sequence of depth maps is at the minimum;
determining that the subject is having the apnea episode in response to the time duration being at least a pre-defined length of time; and
sending a text message to a cellphone of a medical practitioner in response to the determining that the subject is having the apnea episode.

12. The system of claim 11, wherein the target region of the subject comprises at least one of: an anterior thoracic region, a region of a dorsal body, a side view containing a thoracic region, or a view with a sheet covering a body of the subject.

13. The system of claim 11, wherein the camera comprises an image-based depth sensing device comprising any of: a red green blue depth (RGBD) camera, an infrared depth camera, a passive stereo camera, an array of cameras, an active stereo camera, or a monocular video camera.

14. The system of claim 11, wherein the camera comprises any of: a red green blue (RGB) camera, an infrared camera, a multispectral camera, or a hyperspectral camera.

15. The system of claim 11, wherein the pre-defined length of time is at least 20 seconds.

16. The system of claim 11, wherein the analyzing further comprising:
extracting shape descriptors from each of the time-varying sequence of depth maps, the shape descriptors being used for comparison purposes to determine the time duration when a change in shape is at a minimum.

* * * * *